US006827739B2

(12) United States Patent
Griner et al.

(10) Patent No.: US 6,827,739 B2
(45) Date of Patent: Dec. 7, 2004

(54) EASILY ASSEMBLED PROVISIONAL ORTHOPAEDIC IMPLANT

(75) Inventors: Adam M. Griner, Columbia City, IN (US); Douglas G. Branscome, Fort Wayne, IN (US); Marvin Figueroa, Warsaw, IN (US); John Edward Meyers, Columbia City, IN (US); Randy G. Smythe, Tippecanoe, IN (US); Robert Emil Snizek, Warsaw, IN (US); Vincent A. Webster, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 152 days.

(21) Appl. No.: 10/227,739

(22) Filed: Aug. 26, 2002

(65) Prior Publication Data

US 2004/0039450 A1 Feb. 26, 2004

(51) Int. Cl.[7] ............................... A61F 2/28; A61F 2/38
(52) U.S. Cl. .................. 623/16.11; 623/18.11; 623/20.15; 623/20.36; 623/20.33; 623/20.29
(58) Field of Search .................. 623/20.14, 20.15, 623/20.21, 20.23, 20.28, 20.29, 20.13, 20.32, 20.33, 20.34, 20.36

(56) References Cited

U.S. PATENT DOCUMENTS 5,156,626 A    10/1992   Broderick et al. ............ 623/22
5,326,363 A    7/1994    Aikins .......................... 623/20
5,344,461 A    9/1994    Philipot ........................ 623/20
5,458,637 A    10/1995   Hayes ........................... 623/16
6,217,618 B1 * 4/2001    Hileman .................. 623/20.33

OTHER PUBLICATIONS

Nexgen Complete Knee Solution—Revision Instrumentation Surgical Technique For Legacy Constrained Condylar Knee, 1997.

Nexgen Complete Knee Solution—Intramedullary Instrumentation Surgical Technique for Cruciate Retaining Knees, 1998.

* cited by examiner

Primary Examiner—Cary E. O'Connor
Assistant Examiner—Candice C. Stokes
(74) Attorney, Agent, or Firm—Baker & Daniels

(57) ABSTRACT

An easily assembled provisional orthopaedic implant having first and second components. The first component may include a stem which can be inserted into an intramedullary canal and may be a femoral component of a knee joint prosthesis. The second component has a body and a sliding retention member. The retention member can be manually engaged with a groove on the stem of the first component to lock the two components together. The second component may form of an intercondylar box and have a projecting tab engageable with a recess on the femoral component to properly orient the two components when they are placed in registry with each other.

13 Claims, 3 Drawing Sheets

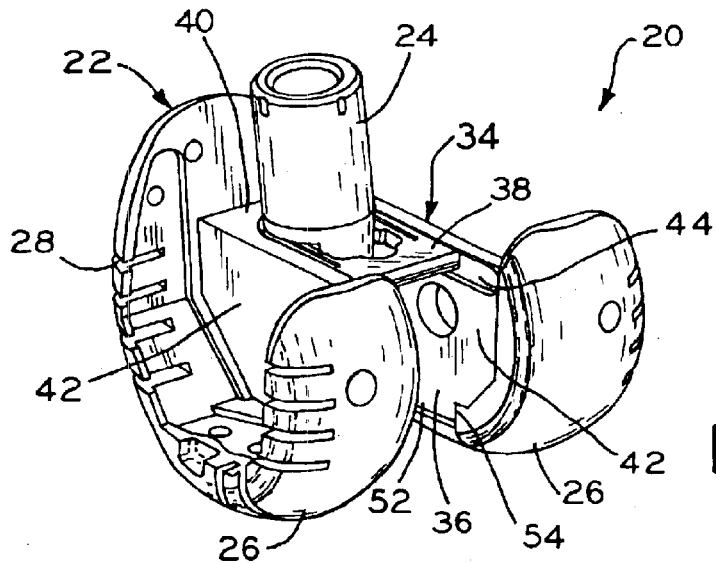
FIG_1
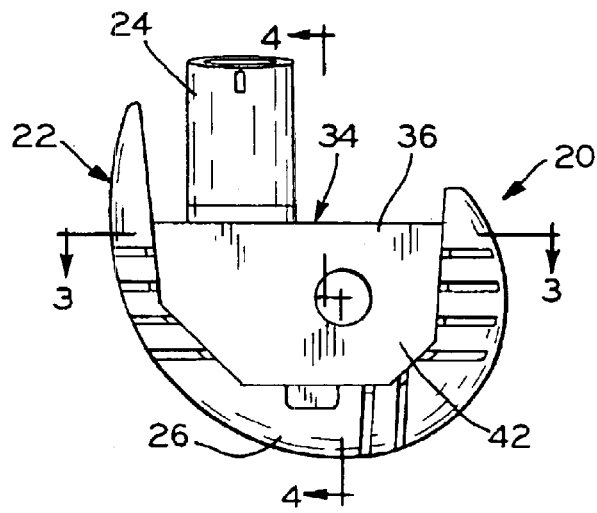
FIG_2
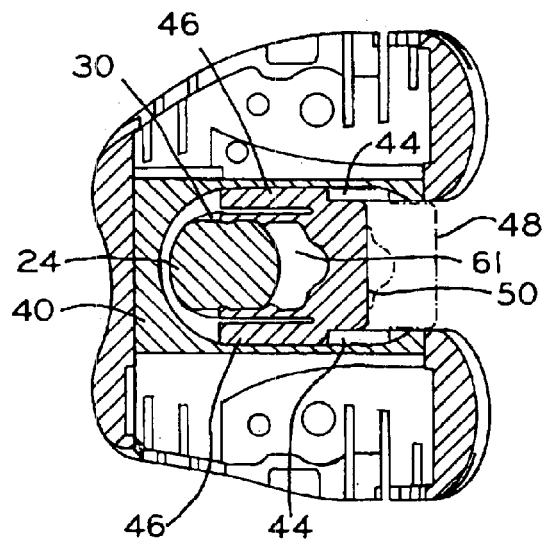
FIG_3

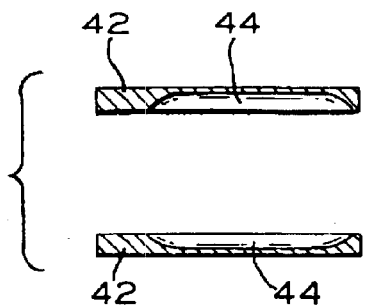
FIG_8
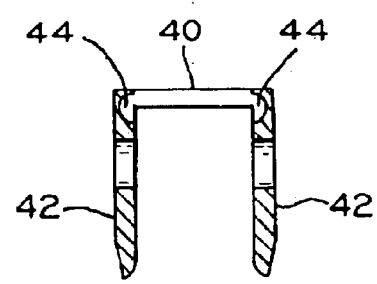
FIG_9
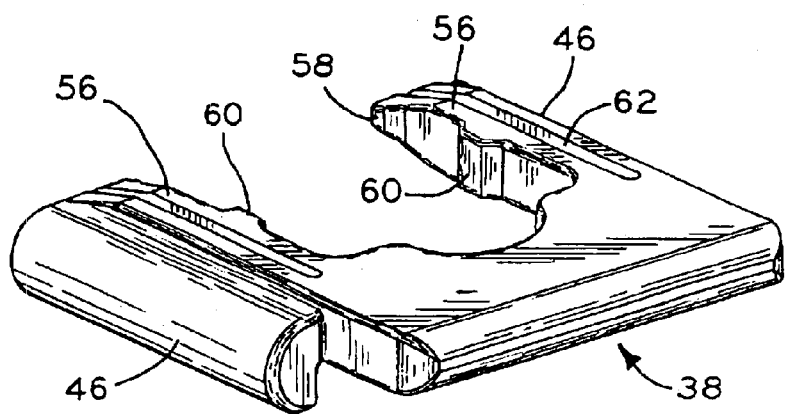
FIG_10
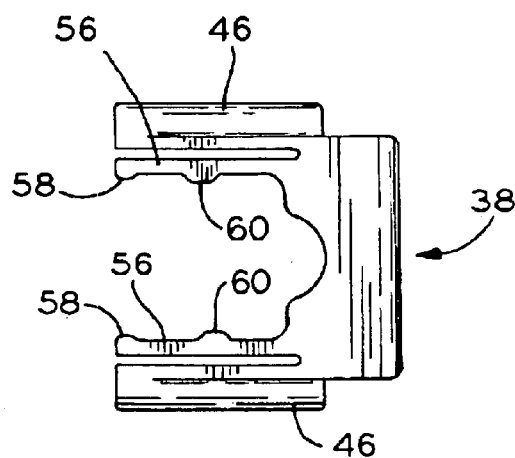
FIG_11

EASILY ASSEMBLED PROVISIONAL ORTHOPAEDIC IMPLANT

BACKGROUND OF THE INVENTION

The present invention relates to orthopaedic implants and, more specifically, to provisional orthopaedic implant components.

The use of implant provisionals is well known in the field of orthopaedic joint replacement surgery. Implant provisionals are often used to test the fit and alignment of an implant with a bone which has been reshaped by a surgeon. The actual implant may also be used for these purposes, however, the use of provisional components during trial fitting and alignment procedures eliminates the risk of damage to the actual implants that may be caused during these procedures.

One common type of joint replacement surgery is knee replacement surgery. For some knee replacement patients, such as those having inadequate mediolateral, anteroposterior and varus-valgus ligament functionality, it is known to use implants which partially constrain the movement of the knee joint to provide enhanced stability. Implants which provide such constrained movement may include an intercondylar box which is implanted in the distal end of the femur.

SUMMARY OF THE INVENTION

The present invention, in one embodiment thereof, provides a provisional orthopedic implant assembly which includes first and second components. The first component has a stem extending therefrom which can be adapted for insertion into an intramedullary canal. The second component has a body and a retention member slidably moveable relative to the body. The retention member is slidable between an unlocked position and a locking position. The second component can be registered with the first component when the retention member is in the unlocked position. Movement of the retention member to the locking position when the second component is in registry with the first component removably secures the second component to the first component.

In alternative embodiments of the invention, the first component is a femoral component which defines a pair of condylar surfaces and the second component is an intercondylar box. The first and second component may be secured together by engagement of the retention member with the stem of the first component. A tab and recess arrangement may also be used to register the first and second components in a desired position. The retention member is advantageously moveable by a manual process which does not require the use of tools (i.e., toolless manual manipulation).

The intercondylar box component may include a central spanning member which interconnects two parallel side walls wherein the inward facing surfaces of the side walls each have a groove and the retention member is slidably mounted in the grooves.

An advantage of the present invention is that it allows for the quick and easy assembly of a provisional device such as a femoral provisional having an intercondylar box. A femoral provisional device having a quickly and easily removable intercondylar box is advantageous in that it allows for the evaluation of the fit of the femoral provisional without an attached intercondylar box prior to cutting the bone which must be removed to allow for introduction of the intercondylar box.

Another advantage is that it provides a provisional assembly which allows for the toolless manual attachment of an intercondylar box to a femoral provisional and thereby eliminates the need to handle small separate fasteners, such as threaded fasteners, when using the provisional assembly.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 1 is a perspective view of a provisional implant assembly in accordance with the present invention.

FIG. 2 is a side view of the provisional implant assembly.

FIG. 3 is a sectional view taken along line 3—3 of FIG. 2.

FIG. 8 is a sectional view taken along line 8—8 of FIG. 7.

FIG. 9 is a sectional view taken along line 9—9 of FIG. 7.

FIG. 10 is a perspective view of a retention member.

FIG. 11 is a plan view of a retention member.

Figure 4:
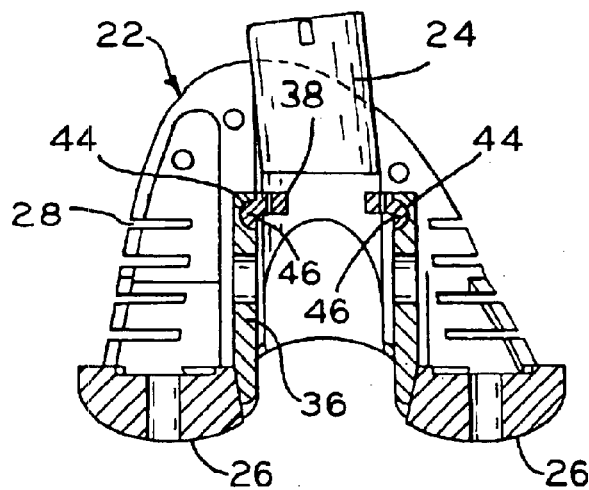
FIG. 4 is a sectional view taken along line 4—4 of FIG. 2.

Corresponding reference characters indicate corresponding parts throughout the several views. Although the drawings represent an embodiment of the present invention, the embodiment described below is set out as an exemplification of the invention and is not intended to be exhaustive or to be construed as limiting the scope of the invention to the precise form disclosed.

DESCRIPTION OF THE PRESENT INVENTION

Figure 5:
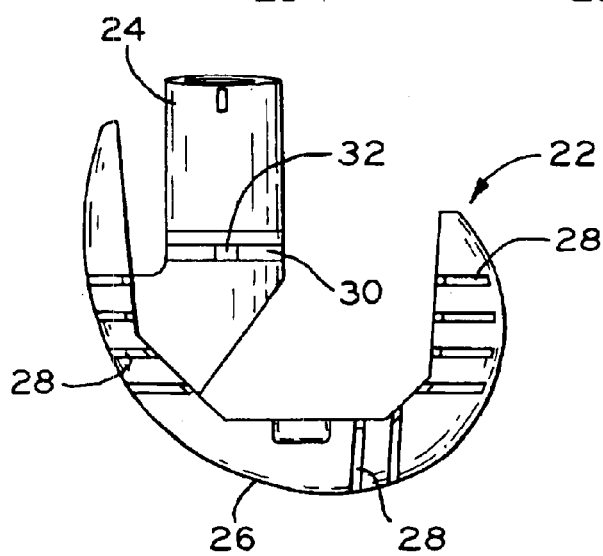
FIG. 5 is a side view of a provisional femoral component.

One embodiment of the present invention is shown in FIG. 1 which illustrates a provisional orthopaedic implant assembly 20. Illustrated assembly 20 includes a femoral component 22 having a stem 24 and a pair of outwardly facing condylar surfaces 26. Stem 24 is adapted to be inserted into an intramedullary canal during a trial fitting procedure and, for a femoral component such as that illustrated in FIG. 1, stem 24 is adapted for insertion into a femoral intramedullary canal. Femoral component 22, which is illustrated in side view in FIG. 5, also includes slots 28 which provide a cutting instrument guide. As best seen in FIGS. 3 and 5, stem 24 also includes grooves 30 located on opposite sides of stem 24. Grooves 30 each include a locking recess 32. The functionality of grooves 30 and locking recesses 32 are discussed in greater detail below.

Figure 6:
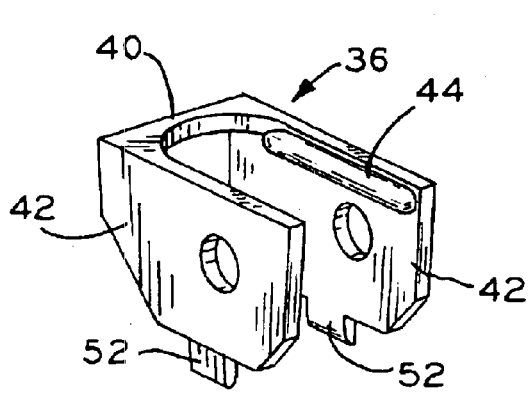
FIG. 6 is a perspective view of the body of a provisional intercondylar box component.
Figure 7:
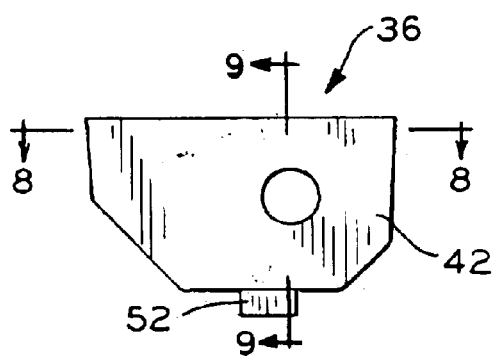
FIG. 7 is a side view of body of FIG. 6.

Also shown in FIG. 1 is a second component 34 having a body portion 36 and a retention member 38 is mounted on femoral component 22. The second component 34 provides a provisional intercondylar box. Body 36 includes a central spanning member 40 which interconnects first and second opposed and substantially parallel side walls 42. As can be seen in FIGS. 4 and 6, each side wall 42 has a groove 44 located on its inward facing surface for mounting retention member 38. Retention member 38 includes outwardly projecting sliding members 46 which are seated within grooves 44 to slidingly mount retention member 38 to body 36. Alternative methods of slidingly mounting retention member 38 to body 36 may also be employed, for example, grooves could be located on retention member 38 and sliding projections could be located on body 36.

As best seen in FIG. 3, retention member 38 may be slid between an unlocked position 48, which is shown in dashed outline in FIG. 3, and a locked position 50. Retention member 38 is placed in the unlocked position 48 to allow stem 24 to be inserted through the opening formed between retention member 38 and central spanning member 40 and for intercondylar box 34 to be placed in registry with femoral component 22. Body 36 includes projecting tabs 52 which interfit with corresponding recesses 54 located on femoral component 22 to properly position intercondylar box 34 on femoral component 22 when placing intercondylar box 34 in registry with femoral component 22.

After placing intercondylar box 34 in registry with femoral component 22, retention member 38 is manually slid from unlocked position 48 to locking position 50 to securely engage intercondylar box 34 to femoral component 22. Retention member 38 includes two resilient members 56 each of which include two engagement projections 58, 60. Gaps 62 are located between sliding members 46 and resilient members 56 to allow resilient members 56 to be biased outwardly as projections 58 of resilient members 56 are first engaged with groove 30 of stem 24 as retention member 38 is moved from unlocked position 48 to locking position 50. When retention member 38 reaches locking position 50, projections 58 are seated in locking recesses 32 located in groove 30 and resilient members 56 snap back into their unbiased positions which are depicted in FIG. 11. In the locking position 50, projections 60 engage stem 24 to inhibit the further movement of retention member 34 towards stem 24 and resist the disengagement of projections 58 and recesses 32.

Although the illustrated stem 24 is adapted for both insertion into an intramedullary canal and for engagement with retention member 34, these two functions could be performed by separate portions of femoral component 22. For example, a groove and locking recess adapted for engagement with a retention member could be located on a different part of the femoral component.

As can be seen in FIG. 3, an opening 61 remains between retention member 38 and stem 24 when the retention member 38 is placed in the locking position 50. Opening 61 facilitates the disengagement of retention member 38 from stem 24 by allowing the insertion of a prying tool between stem 24 and retention member 38 to leverage retention member 38 out of engagement with stem 24 if retention member 38 cannot be disengaged manually.

The use of retention member 38 in illustrated assembly 20 as described above provides a provisional orthopaedic implant which may be easily assembled without requiring the handling of small fasteners and may be used by the surgeon in a manner similar to that of conventional provisional assemblies when performing resection or trial fitting and alignment procedures. The ability to easily assemble a provisional implant assembly 20 facilitates the use of a femoral component 22 without an intercondylar box component 34 while providing for the quick and easy addition of intercondylar box component 34 following use of the femoral component 22 without an intercondylar box component 34 attached thereto.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains. Accordingly, the scope of the invention should be determined not by the illustrated embodiments but by the following claims and their legal equivalents.

What is claimed is:

1. A provisional orthopaedic implant assembly comprising:
   a first component; and
   a second component having a body and a retention member slideably moveable relative to said body, said retention member moveable between a first unlocked position and a second locking position, said second component registerable with said first component when said retention member is in said unlocked position, movement of said retention member to said locking position, with said second component registered with said first component, removably securing said second component to said first component.

2. The assembly of claim 1 wherein said retention member is moveable from said first position to said second position by toolless manual manipulation.

3. The assembly of claim 1 wherein said first component further comprises a stem adapted for insertion into an intramedullary canal and said second component is secured to said first component by engagement of said retention member with said stem when said retention member is in said second position.

4. The assembly of claim 1 wherein said first component further comprises a stem adapted for insertion into an intramedullary canal and said first component defines a pair of condylar surfaces and said stem is adapted for insertion in a femoral intramedullary canal and said second component defines an intercondylar box.

5. The assembly of claim 1 wherein said first component further comprises a stem adapted for insertion into an intramedullary canal and said second component includes a central spanning member interconnecting first and second opposed and substantially parallel side walls, each of said first and second side walls having an inward facing surface respectively defining first and second grooves, said retention member slidingly mounted in said first and second grooves; said second component securable to said first component by engagement of said retention member with said stem when said retention member is in said second position.

6. The assembly of claim 5 wherein said first component defines a pair of condylar surfaces and said stem is adapted for insertion in a femoral intramedullary canal and said second component defines an intercondylar box.

7. The assembly of claim 1 wherein registration of said first and second components comprises the engagement of a tab disposed on one of said components with a recess disposed on the other of said components.

8. A femoral provisional orthopaedic implant assembly comprising:
   a femoral component defining a pair of condylar surfaces and having a stem, said stem being adapted for insertion into a femoral intramedullary canal;
   an intercondylar box component having a body and a retention member slidably moveable relative to said body, said retention member moveable between a first unlocked position and a second locking position, said intercondylar box component registerable with said femoral component when said retention member is in said unlocked position, movement of said retention member to said locking position with said intercondylar box component registered with said femoral component engaging said retention member with said stem and removably securing said intercondylar box component to said femoral component.

9. The assembly of claim 8 wherein said retention member is engageable with a groove defined by said stem.

10. The assembly of claim 8 wherein said retention member is moveable from said first position to said second position by toolless manual manipulation.

11. The assembly of claim 8 wherein said intercondylar box component includes a central spanning member and first and second parallel, opposed side walls, each of said first and second side walls having an inward facing surface respectively defining first and second grooves, said retention member slidingly mounted in said first and second grooves.

12. The assembly of claim 11 wherein said retention member is moveable from said first position to said second position by toolless manual manipulation and said retention member is engageable with a groove defined by said stem when in said second position.

13. The assembly of claim 12 wherein registration of said first and second components comprises the engagement of a tab disposed on one of said components with a recess disposed on the other of said components.

* * * * *